United States Patent
Cote et al.

[19]

[11] Patent Number: 5,913,422
[45] Date of Patent: Jun. 22, 1999

[54] SURGICAL TOOL STERILIZATION AND STORAGE CONTAINER SYSTEM

[75] Inventors: Dwayne R. Cote, Derry; Timothy E. Wood, Weare, both of N.H.

[73] Assignee: Poly Vac, Inc., Manchester, N.H.

[21] Appl. No.: 08/929,238

[22] Filed: Sep. 4, 1997

[51] Int. Cl.⁶ .................................................. B65D 83/10
[52] U.S. Cl. .................... 206/370; 206/210; 206/373; 422/292
[58] Field of Search .................................. 206/370, 439, 206/363, 210, 373, 366, 443, 306; 422/292, 300, 102, 29.7, 104; 220/366.1

[56] References Cited

U.S. PATENT DOCUMENTS

| | | |
|---|---|---|
| 470,567 | 3/1892 | Hitch . |
| 1,451,806 | 4/1923 | Baldridge . |
| 1,519,614 | 12/1924 | Heck . |
| 1,618,027 | 2/1927 | Vogler . |
| 2,971,637 | 2/1961 | Simons . |
| 3,049,946 | 8/1962 | Schelke . |
| 3,102,637 | 9/1963 | Scholl . |
| 3,431,041 | 3/1969 | Fontlladosa . |
| 3,604,565 | 9/1971 | Henkin . |
| 3,743,088 | 7/1973 | Henkin . |
| 3,759,538 | 9/1973 | Fabiano . |
| 4,032,008 | 6/1977 | Vecchiarelli . |
| 4,041,203 | 8/1977 | Brock et al. ............................ 428/157 |
| 4,117,937 | 10/1978 | Ratti . |
| 4,229,420 | 10/1980 | Smith et al. . |
| 4,253,830 | 3/1981 | Kazen et al. . |
| 4,397,395 | 8/1983 | McKelvey . |
| 4,503,972 | 3/1985 | Nelligan et al. . |
| 4,512,498 | 4/1985 | Leibinger . |
| 4,544,351 | 10/1985 | Marsicano . |
| 4,643,303 | 2/1987 | Arp et al. . |
| 4,643,674 | 2/1987 | Zdarsky . |
| 4,671,943 | 6/1987 | Wahlquist ............................. 422/300 |
| 4,728,504 | 3/1988 | Nichols . |
| 4,736,838 | 4/1988 | Nakata et al. . |
| 4,762,688 | 8/1988 | Berry, Jr. . |
| 4,770,297 | 9/1988 | Chang . |
| 4,783,321 | 11/1988 | Spence . |
| 4,798,292 | 1/1989 | Hanze . |
| 4,915,913 | 4/1990 | Williams et al. . |
| 4,922,603 | 5/1990 | Kosmowski . |
| 4,959,199 | 9/1990 | Brewer . |
| 5,004,103 | 4/1991 | Connors et al. . |
| 5,046,624 | 9/1991 | Murphy et al. . |
| 5,048,700 | 9/1991 | Feder . |
| 5,071,346 | 12/1991 | Domaas . |
| 5,098,676 | 3/1992 | Brooks, Jr. . |
| 5,099,992 | 3/1992 | Heimreid . |
| 5,163,549 | 11/1992 | Hayduchok ............................ 206/214 |
| 5,172,810 | 12/1992 | Brewer . |
| 5,174,453 | 12/1992 | Stoeffler . |
| 5,188,242 | 2/1993 | Smith . |
| 5,320,223 | 6/1994 | Allen . |
| 5,358,112 | 10/1994 | Gardner . |
| 5,368,161 | 11/1994 | Plais . |
| 5,490,975 | 2/1996 | Dane ...................................... 422/300 |
| 5,518,115 | 5/1996 | Latulippe . |
| 5,525,314 | 6/1996 | Hurson . |
| 5,716,584 | 2/1998 | Baker et al. ............................ 422/131 |

FOREIGN PATENT DOCUMENTS

| | | |
|---|---|---|
| 1364546 | 1/1988 | U.S.S.R. . |
| 2198119 | 6/1988 | United Kingdom . |

*Primary Examiner*—Paul T. Sewell
*Assistant Examiner*—Nhan T. Lam
*Attorney, Agent, or Firm*—Hayes, Soloway, Hennessey, Grossman & Hage, P.C.

[57] ABSTRACT

A sterilization tray container system includes an apertured rack in which surgical tools are located. A resiliently deformable retention mat having a plurality of apertures formed in a predetermined array pattern underlying, at least in part, the array pattern in the tray, is provided below the rack. The apertures in the resiliently deformable retention mat extend entirely therethrough, and are sized and configured so as to releasably grip the surgical tools intended to be placed therein. The resiliently deformable retention mat is positioned below the rack, and is attached to the rack by a mechanical support, or fixedly held in position between the rack and the container bottom.

10 Claims, 7 Drawing Sheets

SURGICAL TOOL STERILIZATION AND STORAGE CONTAINER SYSTEM

FIELD OF THE INVENTION

The present invention relates to container systems for tools and, more particularly, to a surgical container system for the organization, sterilization, and safe storage of delicate surgical instruments such as dental implantation tools (e.g. burrs and insertion wrenches).

BACKGROUND OF THE INVENTION

Many surgical procedures require a specific, specialized group of surgical tools with any one procedure potentially requiring anywhere from just a few to literally dozens of individual tools. The tools must be sterilized and presented at the surgical site in a manner facilitating quick selection and retrieval of a needed tool by the medical practitioner during the surgical procedure. This is especially true in the dental arts, where many dental instruments are typically used in quick succession during one procedure. For example, a dental implant procedure normally requires the sequential use of several dental burrs (i.e. drills) of increasingly larger diameter, in addition to the intermediate and/or subsequent use of other implant tools (i.e. implant component insertion and extraction tools).

Container systems have been developed in the past which organize, sterilize, store and present a specific group of tools for a dental or other surgical procedure, all in the same container. In this regard, it is normally intended that the surgical tool container system organize a group of tools in a manner allowing the medical practitioner to retrieve the needed tools directly from the container during the surgical procedure. Examples of such containers may be seen in U.S. Pat. No. 5,098,676 to Brooks. Unfortunately, these as well as other prior container systems of their kind have given little attention to at least two very important considerations of such containers: (1) securing the tools in the container in a manner substantially preventing the accidental dislodgment of the tools from their original place within the container regardless of container orientation; (2) the ease by which a medical practitioner can quickly identify, select and then remove the needed tool from a group of tools within the container during a surgical procedure.

Regarding the first consideration, during normal handling the container may be inverted from its correct orientation, thus potentially disturbing the organization of the tools within the container. Should this occur, valuable time is spent on re-organizing the tools within the container prior to the surgical procedure, and hopefully without the need for re-sterilization should some of the tools fall entirely out of the container. The container thus preferably includes means to securely retain the tools in their organized position within the container, regardless of the orientation of the container.

Regarding the second consideration, the medical practitioner needs to be able to identify, select and remove the needed tool from the container quickly and easily, and advantageously with the use of a single hand.

Since the tools are sterilized in the same container in which they are stored and used in surgery, the container must be very durable so as to withstand repeated sterilization cycles and handling. While the container must be durable and include features to securely retain the tools in their position within the container, those features must not conflict with the need for quick identification and retrieval of a tool from the container. Also, once the surgical procedure is finished, the tools must be replaced in their original positions within the container. Thus, it is furthermore desirable that the features which permit the secure retention of the tools within the container also permit quick and easy replacement of those same tools back in their original positions in the container. These features provide a container system in which the group of tools may be quickly reorganized for subsequent sterilization, storage and use cycles.

The foregoing discussion of the prior art was taken largely from U.S. Pat. No. 5,525,314 to Hurson in which there is disclosed surgical tool sterilization trays provided with a plurality of holes formed therethrough and wherein the plurality of elastomeric grommets are fitted into the holes. According to the '314 patent, each grommet includes an axially extending bore wherein the shank of a surgical tool may be inserted and frictionally engaged in a gently upright orientation with respect to the tray. The grommets reportedly removably secure the tools in their original positions within the container regardless of container orientation, yet permit the quick and easy removal of a tool from the container during a surgical procedure, as well as equally quick and easy replacement of the tool within the container for subsequent sterilization and use cycles. See, also, U.S. Pat. No. 5,518,115 to Latulippe which discloses an alternative grommeted surgical tray arrangement.

While surgical tray systems such as disclosed in U.S. Pat. Nos. 5,525,314 and 5,518,115 meet the above considerations, such patented trays do have certain disadvantages. For one, assembling the many grommets into the tray is tedious and time-consuming, thus adding to production costs. Also, the grommets tend to mask areas on the base plate or tray, both under the heads of the grommets and in the walls of the apertures in the trays, thus providing potential sites for condensation and contamination traps.

SUMMARY OF THE INVENTION

The present invention overcomes the aforesaid and other disadvantages of the prior art, and achieves the above needs, by providing a sterilization tray container system including an apertured rack in which surgical tools are located. A resiliently deformable retention mat having a plurality of apertures formed in a predetermined array pattern underlying, at least in part, the array pattern in the tray, is provided below the rack. The apertures in the resiliently deformable retention mat extend entirely therethrough, and are sized and configured so as to releasably grip the surgical tools intended to be placed therein. The resiliently deformable retention mat is positioned below the rack, and may be attached to the rack, e.g. by a mechanical support, or fixedly held in position between the rack and the container bottom.

BRIEF DESCRIPTION OF THE DRAWINGS

Other features and advantages of the present invention will be seen from the following detailed description, taken in conjunction with the accompanying drawings, wherein like numerals depict like parts, and wherein.

DETAILED DESCRIPTION OF THE PREFERRED EMBODIMENT

Figure 1:
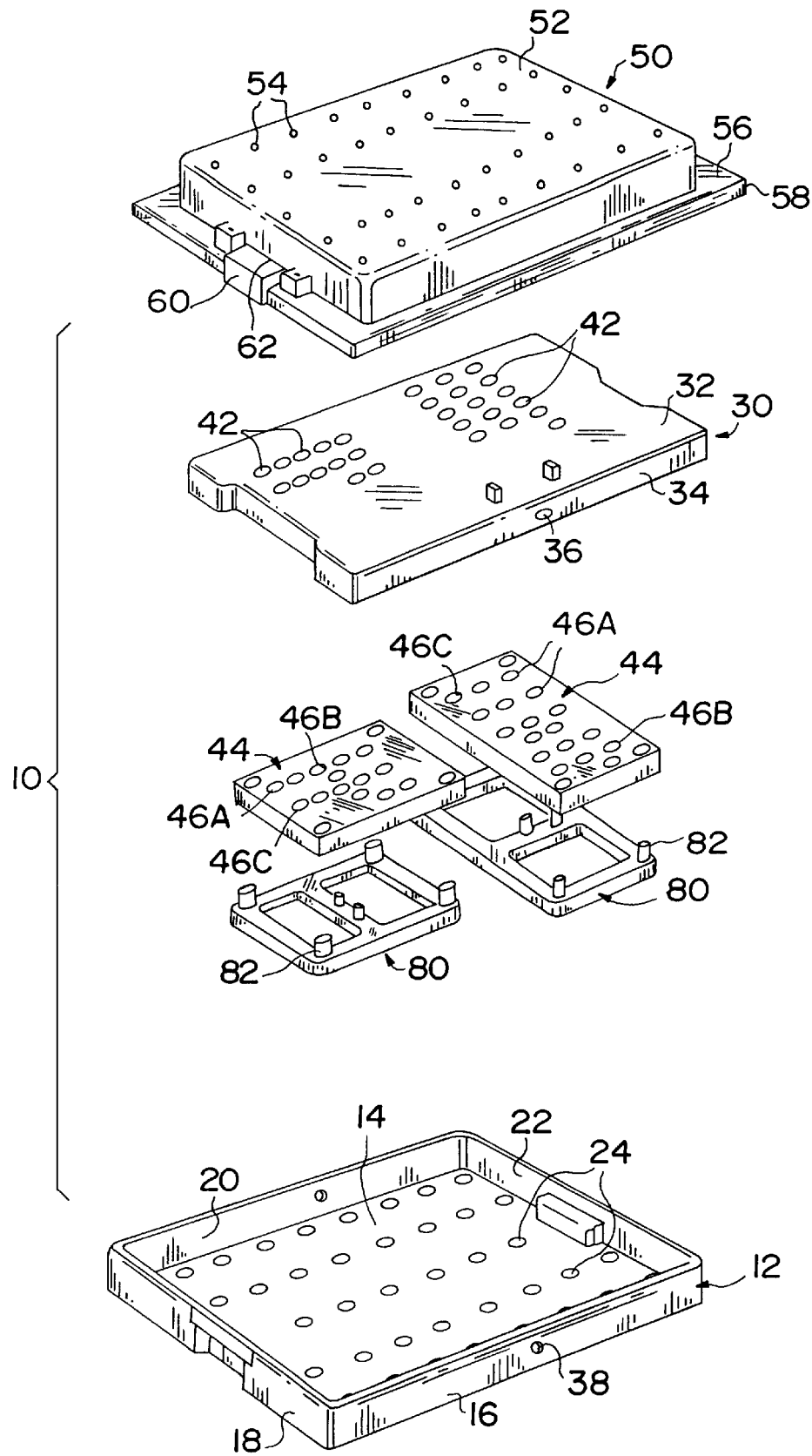
FIG. 1 is a exploded perspective view of a surgical tool sterilization and container system made in accordance with the present invention.
Figure 2:
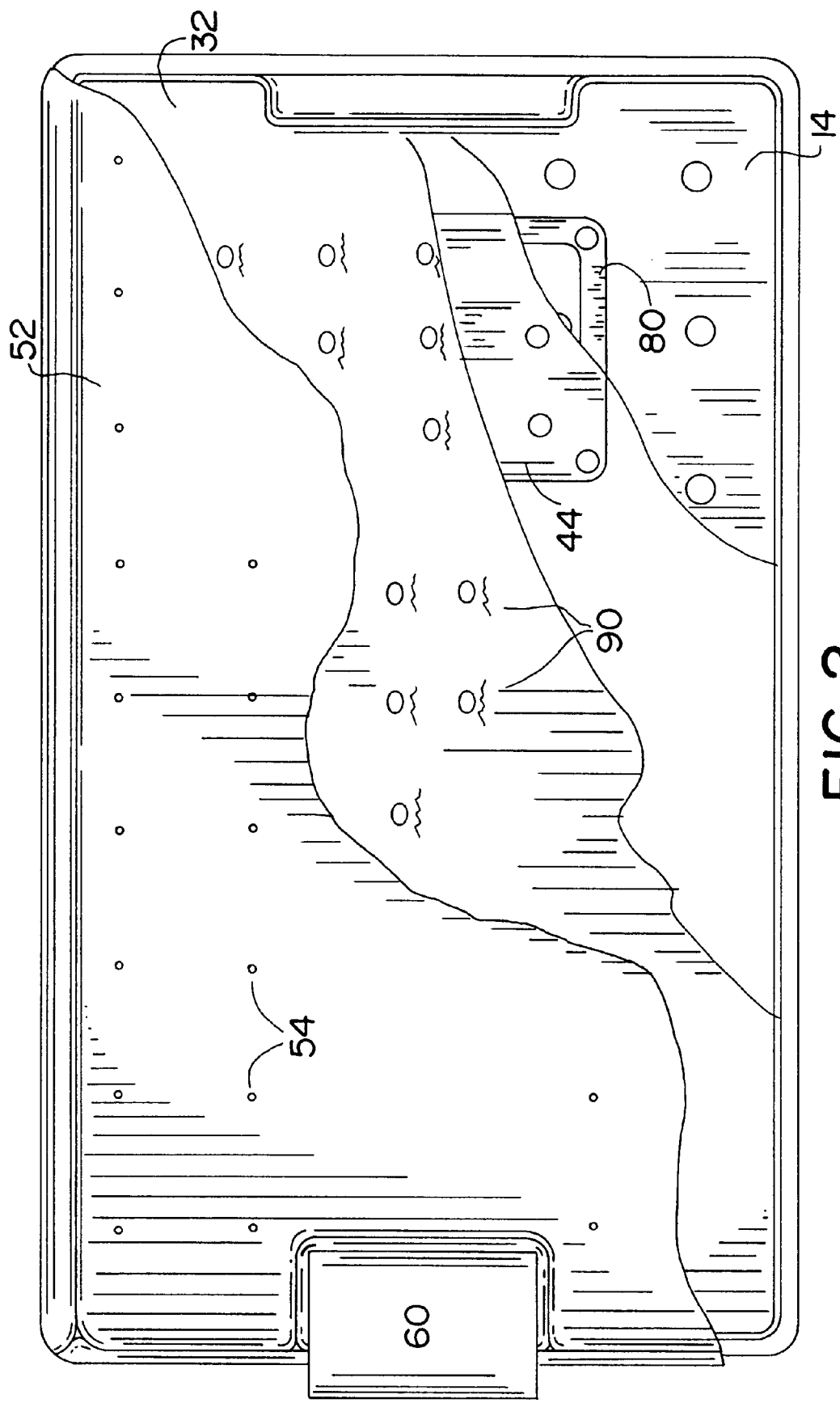
FIG. 2 is a top plan view of the sterilization and storage container system of FIG. 1, shown partly broken away.
Figure 3A:
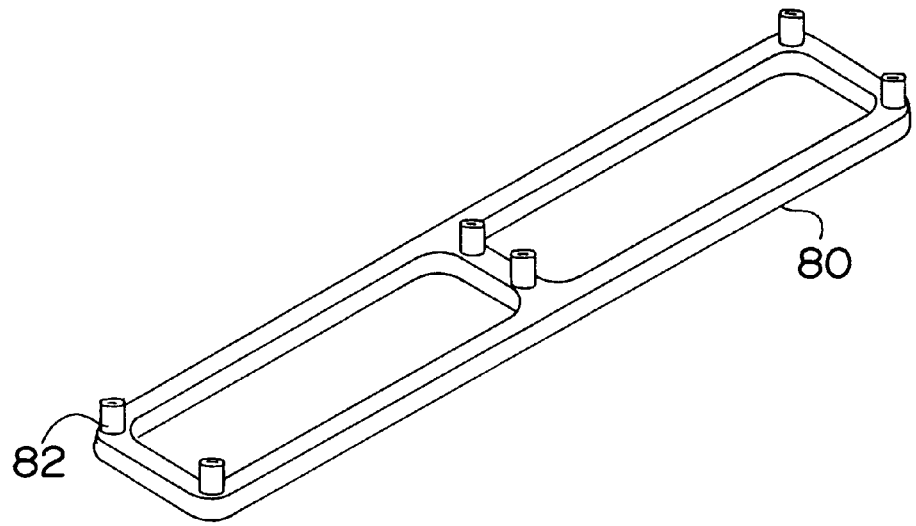
FIGS. 3A–3C are three views of one of the retention plate frame member portion in accordance with one embodiment of the invention.
Figure 3B:
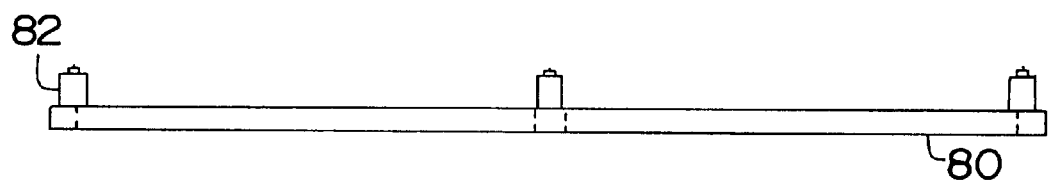
Figure 3C:
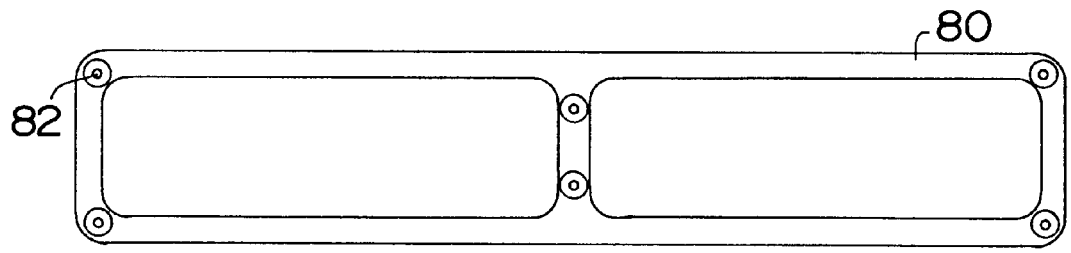

Referring now to the drawings, and in particular to FIGS. 1–3, the sterilization, transporting and storage tray assembly of the present invention is indicated generally by numeral 10. The tray assembly 10 consists of a box-like bottom tray 12 having a bottom 14 and four generally perpendicular upwardly projecting continuous sidewalls comprising a front sidewall 16, a left sidewall 18, a back sidewall 20 and a right sidewall 22. Tray bottom 14 includes a plurality of spaced apertures 24 arranged in a predetermined pattern. Apertures 24 permit ingress and egress of steam or other gaseous sterilants, and allow for condensation drainage.

An instrument support rack 30 having a generally planar top surface 32 and a downwardly projecting lip 34 which forms the periphery of rack 30, is inserted in, and rests within base 12. Rack 30 is mounted within base 12 spaced from the base side walls 16, 18, 20 and 22, for example, by a pair of raised tabs or detents 36 which cooperate with proximately located apertures 38 in the base side walls 16 and 18 whereby to form a gap between the periphery of lip 34 and the inside of walls 16, 18, 20 and 22. The gap permits ingress and egress of steam or other gaseous sterilants and allows for condensation drainage.

A feature and advantage of the present invention is to provide a surgical instrument delivery system for pre-defined surgical procedures in which a selection of tools with a range of sizes and styles may be prepackaged for use in a logical sequence of operations. For example, as applied to dental implant surgery, a typical sequence of steps may comprise first drilling a pilot hole, for example, in the jaw bone; the pilot hole is then enlarged, and the hole then threaded using a thread former. Threaded pins are then mounted in the threaded holes using a driver. As will be appreciated these various tools comprise different diameters. While the holes for accommodating the instruments may be custom drilled, i.e. to accommodate instruments of different diameters, in a preferred embodiment of this invention, in order to facilitate manufacture of the rack, a plurality of holes 42, are drilled in the rack in a predetermined layout, and a resiliently deformable mat 44 having through-holes 46A, 46B, 46C . . . which may be the same size, or different size, e.g. to accommodate different sized instruments, is located under tray 30. Holes 46A, 46B, 46C . . . should be drilled completely through resilient pad 44 so as to promote drainage. In other words, holes 46A, 46B, 46C . . . should not be blind holes. Holes 46A, 46B,46C . . . should correspond to the layout of holes 42 in rack 30. Mat 44 should be formed of a resiliently deformable elastomeric material that maintains its resiliency over repeated temperature cycling, and is approved for medical sterilization uses, for example, silicon rubber or the like.

Figure 4:
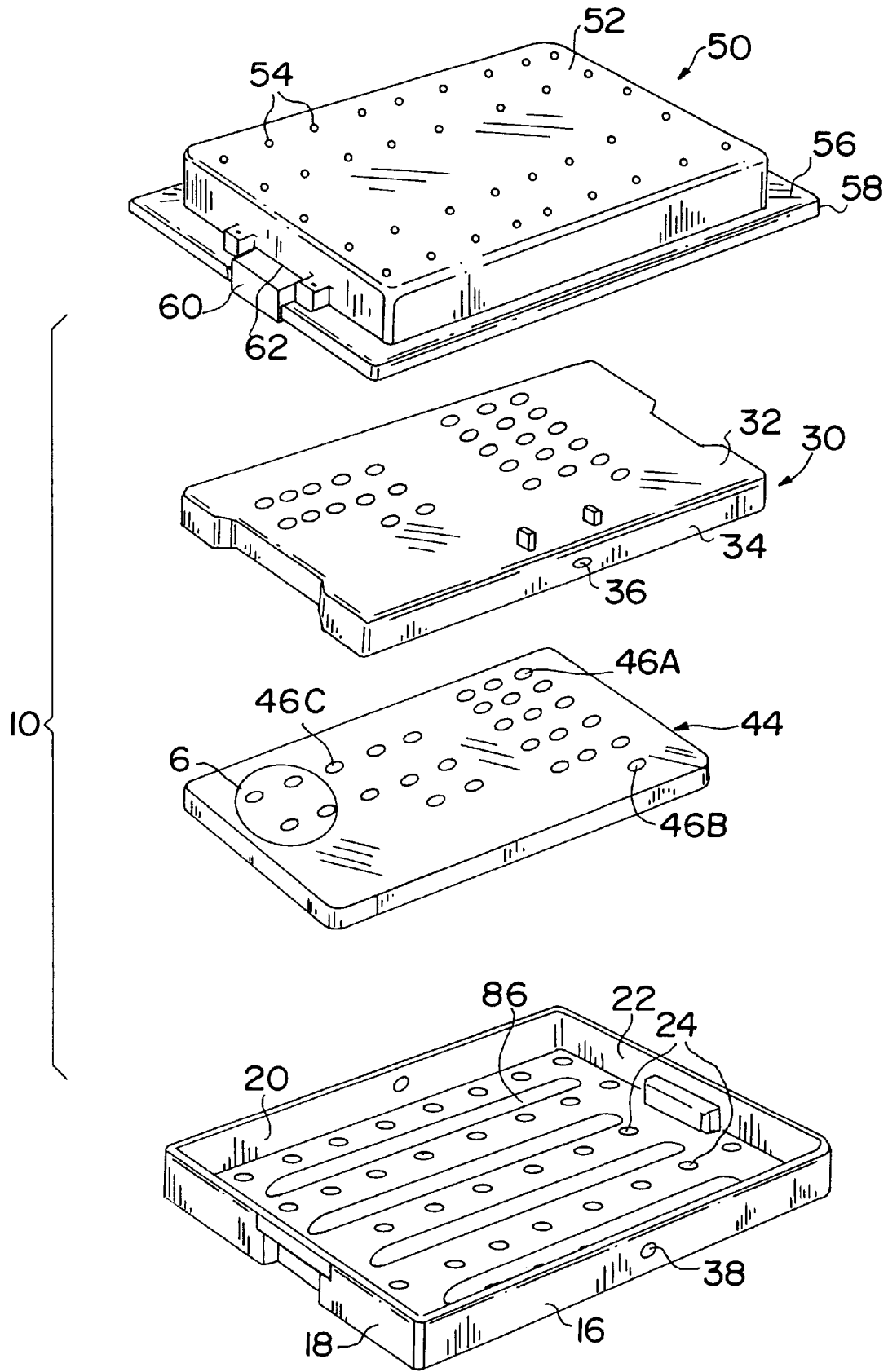
FIG. 4 is a view similar to FIG. 1, and showing an alternative embodiment of surgical tool sterilization and container system made in accordance with the present invention.
Figure 5:
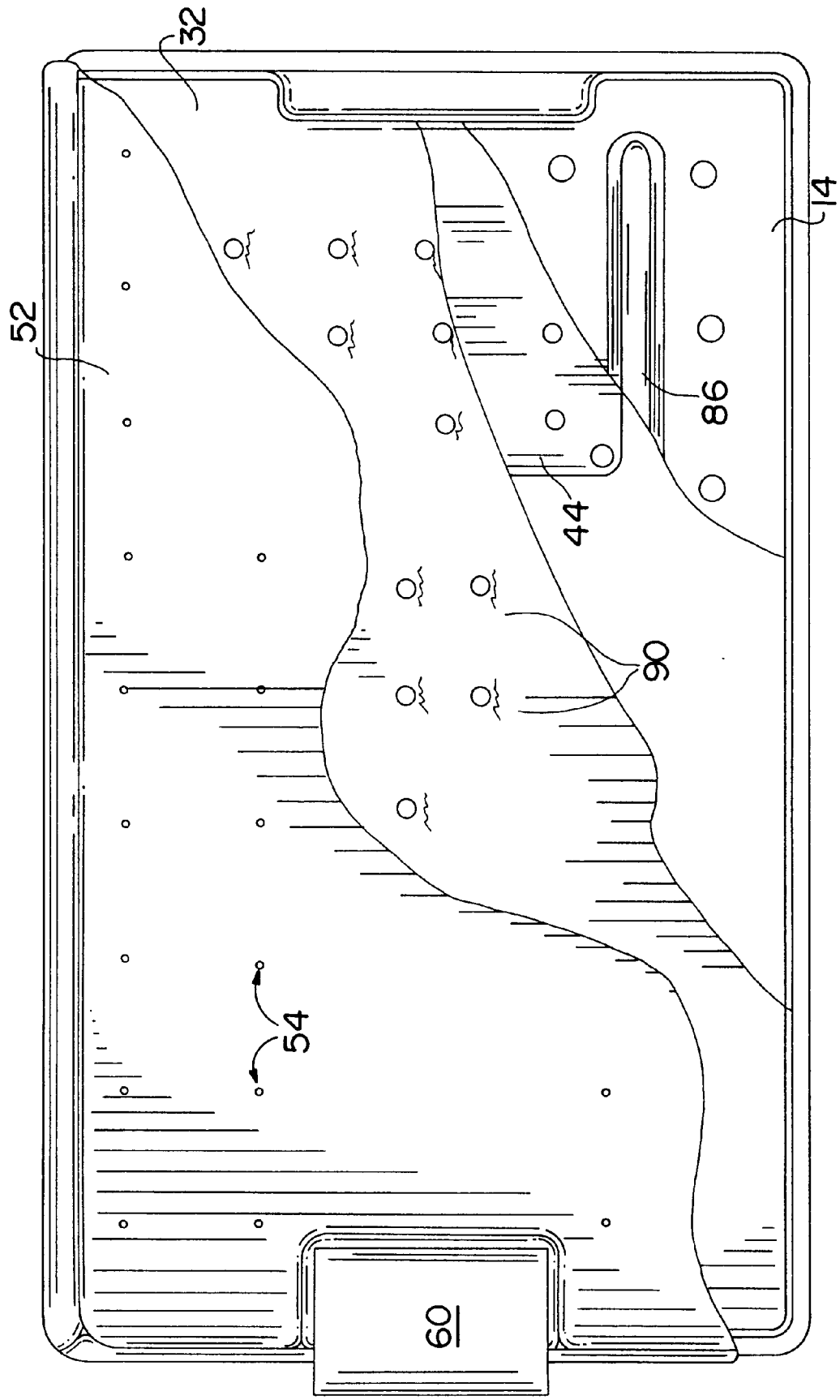
FIG. 5 is a top plan view of the sterilization and storage container system of FIG. 4, shown partly broken away.
Figure 7:
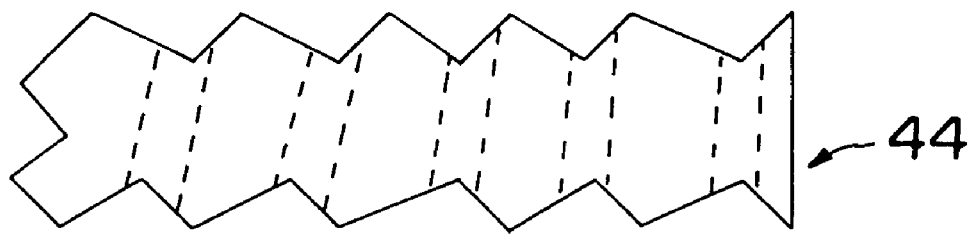
FIG. 7 is a cross-sectional view of the retention plate portion of an alternative embodiment of the invention.

Resilient mat 44 preferably is fixedly held in position, to the bottom of rack 30, by means of a frame or rail system 80, which preferably includes a plurality of integral standoffs 82 which may be ultrasonically welded or chemically or adhesively bonded to the bottom of rack 30 so as to fixedly position the resilient mat 44. Alternatively, as shown in FIGS. 4 and 5, resilient mat 44 may be held in position sandwiched between the bottom of rack 30 and the top of tray base 12. In such case, base 12 preferably will include a plurality of upwardly directed ridges or bumps 86 for supporting a mat 44 off the surface of tray base 12, and to assist in condensation drainage. If desired, resilient mat 44 may be serrated, i.e. as shown in FIG. 7 so as to minimize the area of contact between the mat and the bottom of rack 30, rails 84, and tray base 12, as the case may be.

Figure 6:
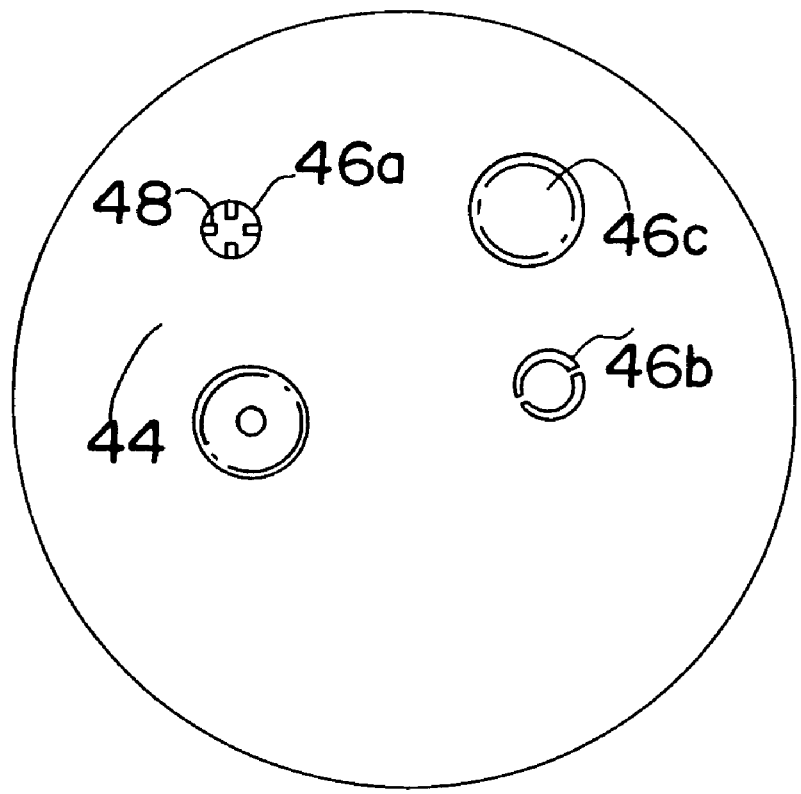
FIG. 6 is an enlarged top plan view of a portion of FIG. 4.

Referring in particular to FIG. 6, if desired, a plurality of inwardly extending projections or ribs 48 may be formed on the inside wall surfaces 49 of the holes 46 in resilient mat 44. As shown in FIG. 6, ribs 48 are equi-spaced around the periphery of holes 46. While four ribs 48 are shown in FIG. 6, as few as three ribs, or five or more ribs may be provided.

Preferably, but not necessarily, indicia 90 may be printed adjacent the various holes in rack 30, identifying the individual tools; also, if desired, duplicate tools may be arranged adjacent one another on the tray.

Top 50 is of a box-like shape and includes a top surface 52 having a plurality of spaced apertures 54 arranged around the periphery of the top surface 52 to permit the ingress and egress of steam or other gaseous sterilants during sterilization, and drainage of condensation from the top surface 52. Top 50 includes an outwardly projecting peripheral ridge section 56, and a downwardly projecting lip section 58 which together engage the top portions of walls 16, 18, 20 and 22 of base 12 when the top 50 is locked upon the base 12. If desired, an instrument key, such as a drill depth guide or other indicia may be printed on the inside surface of the top cover 50.

Completing the sterilization and storage container tray of the present invention are C-shaped locking hinges 60 made of a flexible metal or plastic which are attached to top 50 by hinge pins 62 at the midpoint position of the opposite ends of top 50.

Figure 8A:
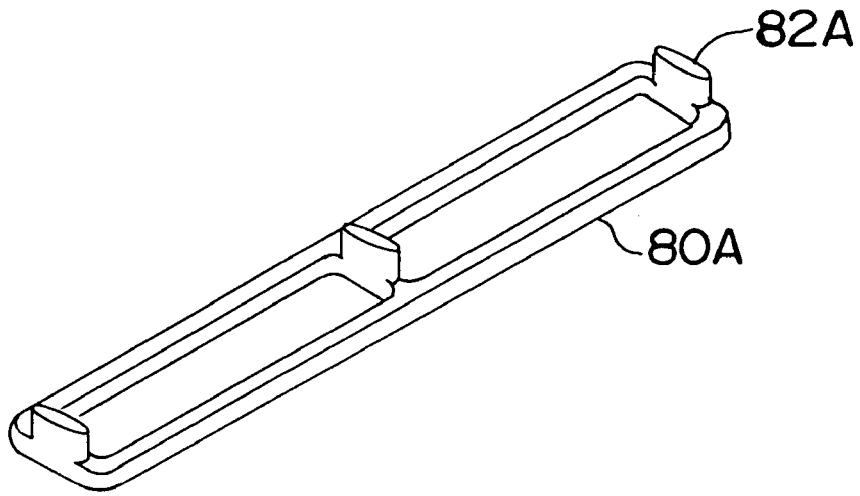
FIGS. 8A–8C are three views of another form of retention plate frame member portion in accordance with another embodiment of the invention.
Figure 8B:
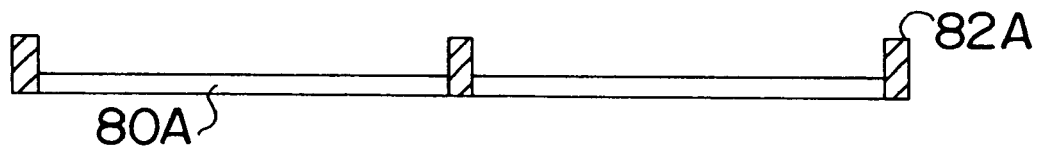
Figure 8C:
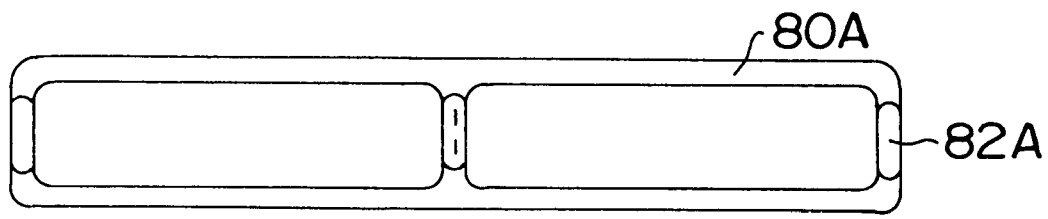

FIGS. 8A–8C illustrate an alternative design of frame or rail system 80A and comprising integral standoffs 82A, for supporting a suitable dimensioned resilient mat.

While particular embodiments of the present invention have been illustrated and described herein, it is not intended to limit the invention, and changes and modifications may be made therein without departing from the scope of the invention.

We claim:

1. In a sterilization tray assembly for sterilizing, transporting and storing surgical instruments, comprising top and bottom mating enclosures, said mating enclosures each comprising a plurality of ports for permitting ingress and egress of gaseous sterilant, and a rack dimensioned to fit within the bottom enclosure, said rack having a plurality of spaced apertures for receiving a selected surgical instrument therein, and means for locking said mating enclosures to one another, the improvement which comprises a retention pad, formed of a resiliently deformable material, located in fixed position under said rack, said retention pad having a plurality of drilled through-holes, sized and configured so as to releasably grip surgical instruments placed therein.

2. In a tray assembly according to claim 1, the improvement wherein at least some of the through-holes in the retention pad have different diameters for accommodating different diameter instruments.

3. In a tray assembly according to claim 1, the improvement wherein at least some of the through-holes in the retention pad include a plurality of inwardly directed ribs for gripping surgical instruments therein.

4. In a tray assembly according to claim 1, and further including an indicia key to surgical instruments printed on the rack.

5. In a tray assembly according to claim 1, the improvement wherein said resiliently deformable retention pad is supported in contact with the bottom of said rack, by a frame.

6. In a sterilization tray assembly according to claim 1, the improvement wherein said resiliently deformable retention plate is sandwiched between the bottom of said rack and the bottom mating enclosure.

7. In a sterilization tray assembly according to claim 6, the improvement wherein the resiliently deformable retention plate is supported above the bottom mating enclosure on bumps or ridges.

8. In a tray assembly according to claim 1, the improvement wherein the resiliently deformable retention pad has at least one serrated surface.

9. In a tray assembly according to claim 1, the improvement wherein the resiliently deformable retention pad is formed of silicon rubber.

10. In a tray assembly according to claim 1, the improvement wherein at least some of the drilled through-holes in the retention pad are aligned at least in part with the spaced apertures in the rack.

* * * * *